United States Patent [19]
Callan

[11] Patent Number: 6,024,567
[45] Date of Patent: Feb. 15, 2000

[54] DENTAL PROSTHESIS

[76] Inventor: Donald P. Callan, 39 Hickory Hills Cir., Little Rock, Ark. 72212

[21] Appl. No.: 09/288,337

[22] Filed: Apr. 8, 1999

Related U.S. Application Data

[63] Continuation-in-part of application No. 09/041,525, Mar. 12, 1998, Pat. No. 5,931,675, which is a continuation-in-part of application No. 08/679,223, Jul. 12, 1996, abandoned.

[51] Int. Cl.[7] .................................................. A61C 8/00
[52] U.S. Cl. ............................................................ 433/173
[58] Field of Search .................................. 433/173, 174, 433/175, 176, 172

[56] References Cited

U.S. PATENT DOCUMENTS

| | | | |
|---|---|---|---|
| 4,252,525 | 2/1981 | Child | 433/173 |
| 4,668,191 | 5/1987 | Pischka | 433/174 |
| 4,932,868 | 6/1990 | Linkow | 433/174 |
| 4,934,935 | 6/1990 | Edwards | 433/174 |
| 5,049,073 | 9/1991 | Lanks | 433/173 |
| 5,102,336 | 4/1992 | Linkow | 433/176 |
| 5,316,477 | 5/1994 | Calderon | 433/173 |
| 5,549,475 | 8/1996 | Duerr | 433/173 |
| 5,620,323 | 4/1997 | Bressman | 433/174 |
| 5,931,675 | 8/1999 | Callar | 433/173 |

FOREIGN PATENT DOCUMENTS 2734369  7/1988  France .

*Primary Examiner*—Nicholas D. Lucchesi
*Attorney, Agent, or Firm*—Stetina Brunda Garred & Brucker

[57] ABSTRACT

A dental prosthesis comprising an implant, an abutment attached to the implant in a manner wherein an implant abutment joint is defined therebetween, and a crown attached to the abutment and the implant in a manner wherein the implant abutment joint is covered by the crown. The attachment of the crown to the abutment and the implant is accomplished through the use of an adhesive which extends between the crown and the implant in a manner wherein the adhesive seals the implant abutment joint thereby preventing any bacterial colonization or other deterioration therein.

20 Claims, 2 Drawing Sheets

DENTAL PROSTHESIS

RELATED APPLICATIONS

The present application is a continuation-in-part of U.S. application Ser. No. 07/041,525 filed Mar. 12, 1998, now U.S. Pat. No. 5,931,675, which is a continuation-in-part of U.S. application Ser. No. 08/679,223 entitled DENTAL PROSTHESIS filed Jul. 12, 1996, now abandoned the disclosure of which is incorporated herein by reference.

FIELD OF THE INVENTION

The present invention relates generally to dental prostheses and, more particularly, to a dental prosthesis including an implant, an abutment which is attached to the implant, and a crown which is attached to both the abutment and the implant such that the joint defined between the abutment and the implant is covered and affectively sealed by a prosthetic margin of the crown.

BACKGROUND OF THE INVENTION

As is well known in the prior art, dental prostheses are commonly used in the dental field to address extensive damage to teeth caused by injury or disease. A typical dental prosthesis comprises an implant, an abutment, and a crown. The implant itself generally comprises a metallic component which is implanted or embedded into the bony structure of a patient's mouth subsequent to the removal of the damaged tooth or teeth alone or in combination with one or more adjacent teeth. The installation of the implant is typically accomplished by preparing a hole in the bony structure and screwing threads formed on the implant into the hole. After the implant has been embedded into the bony structure, the bone normally recovers and grows around the implant, thus resulting in bone/implant integration. To enhance the integration of the bone thereto, the implant may be coated with a biocompatible coating such as hydroxylapatite.

Subsequent to the embedding of the implant into the bony structure, the abutment is attached to the implant. Such attachment may be accomplished through the use of a cement, the engagement of complementary male and female threads formed on or in the abutment and implant, or the mating of corresponding tapers or other geometries formed on or in the abutment and implant. When attached to the implant, a portion of the abutment extends above the gum line of the patient for purposes of allowing the attachment of the crown thereto. If the implant is embedded in the bony structure such that the same is completely disposed below or submerged within the gum line of the patient, the attachment of the abutment to the implant requires a second surgical procedure for purposes of accessing the implant. However, if the implant is embedded in the bony structure in a manner wherein a portion thereof protrudes above the patients gum line, then the attachment of the abutment thereto may be accomplished without the need for the second surgical procedure, thus requiring only the initial surgical procedure to complete the implantation or embedding process.

As previously indicated, the crown of the dental prosthesis is attached to that portion of the abutment which extends above the patient's gum line. In the prior art, crowns are fabricated and installed in accordance with well-established procedures which include taking a transfer impression of the exposed portion of the abutment to establish with precision its configuration and orientation, thus insuring a complete attachment of the crown thereto. The exposed portion of the abutment to which the crown is attached may have the natural form of a prepared tooth, or an artificial form of a particular geometry adapted to achieve a secure attachment of the crown thereto. The attachment of the crown to the abutment is typically accomplished through the use of a cement, or through the engagement of corresponding male and female threads on or in the crown and abutment to each other. The attachment of the crown to the abutment completes the assembly of the dental prosthesis.

As will be recognized from the aforementioned description of the dental prosthesis, the assembly thereof results in the formation of several distinct joints. These joints include the joint formed by the attachment of the crown to the abutment, and the joint formed by the attachment of the abutment to the implant. Of these joints, that joint considered most important in relation to the long-term viability of the prosthesis is the joint between the implant and the abutment which is commonly referred to as the implant abutment joint or "IAJ".

Recent research in the dental field has suggested that the IAJ plays a key role in bone loss around the implant. Though such bone loss has not been well studied or well documented, it is believed by the dental profession to be a common occurrence which is at least partially attributable to the IAJ serving as a site for bacterial invasion and colonization. Over time, such bone loss can compromise the implant or cause its failure by breaking loose from the bony structure in which it is implanted or embedded. Obviously, such failure, in addition to providing inconvenience and discomfort for the patient, is of serious medical concern due to the resulting bone loss or mutilation potentially rendering the installation of a replacement implant difficult or impossible. The joint formed by the attachment of the crown to the abutment is also susceptible to bacterial invasion which contributes to bone loss around the implant. The present invention addresses the susceptibility of the IAJ and the crown/abutment joint to bacterial infestation by providing a dental prosthesis which is configured to effectively cover and seal these joints.

SUMMARY OF THE INVENTION

In accordance with the present invention, there is provided a dental prosthesis which comprises an implant adapted to be embedded into the bony structure of a patient's mouth. The dental prosthesis further comprises an abutment which is attached to the implant in a manner wherein an abutment joint is defined therebetween. In addition to the implant and the abutment, the dental prosthesis comprises a crown which is attached to the abutment and to the implant in a manner wherein the implant abutment joint is covered by the crown. The attachment of the crown to the abutment and the implant is accomplished through the use of an adhesive which extends between the crown and the implant in a manner wherein the adhesive seals the implant abutment joint and the joint formed between the crown and the implant. In this respect, the adhesive effectively isolates these joints from the gum line of the patient to prevent any migration of bacteria thereto.

In the preferred embodiment, the implant itself includes an elongate, externally threaded implant distal portion which is insertable into the bony structure of the patient's mouth, and an implant proximal portion which itself includes distal and proximal segments. The distal segment of the implant proximal portion has a generally cylindrical outer surface, with the proximal segment having a beveled or tapered outer surface in one embodiment of the present invention, and a generally cylindrical outer surface of a lesser diameter than the outer surface of the distal segment in another embodiment of the present invention. The proximal segment defines an implant proximal end of the implant. Extending axially within the implant proximal end is an implant aperture which has a generally circular cross-sectional configuration.

The abutment of the dental prosthesis includes an abutment proximal portion which has a generally frusto-conical outer surface. As such, the general shape of the abutment proximal portion is that of a truncated cone. Extending axially from the end of the abutment proximal portion of greater diameter is a cylindrically configured, shaft-like abutment distal portion of the abutment. The attachment of the abutment to the implant is facilitated by the slidable insertion of the abutment distal portion into the implant aperture. The advancement of the abutment distal portion into the implant aperture is limited by the engagement of the abutment proximal portion to the implant proximal end. In one embodiment of the present invention, the abutment distal portion is secured within the implant aperture through the use of an adhesive. In another embodiment of the present invention, the implant aperture is internally threaded, with the abutment distal portion being externally threaded and the attachment of the abutment to the implant being facilitated by the threadable receipt of the abutment distal portion into the implant aperture.

The crown of the present dental prosthesis includes a crown distal portion which defines a crown distal end having a crown aperture disposed therein. The crown aperture has a shape which is complementary to the outer surface of the abutment proximal portion and the outer surf ace of the proximal segment of the implant proximal portion when the abutment is attached to the implant. In this respect, the receipt of the abutment proximal portion and the proximal segment of the implant proximal portion into the crown aperture results in the engagement of the crown distal portion to the proximal segment of the implant proximal portion (i.e., the direct contact therebetween) and the covering of the implant abutment joint defined between the abutment proximal portion and the implant proximal end by the crown distal portion. The adhesive used to secure the crown to the abutment and the implant flows or extends between the crown distal portion and the tapered outer surface of the proximal segment of the implant proximal portion, thus effectively sealing the joint between the crown and the implant, and hence the implant abutment joint as well as the joint between the crown and the abutment.

In the embodiment of the implant wherein the proximal segment of the implant proximal portion has the tapered outer surface, the attachment of the abutment to the implant in the above-described manner results in the sloped outer surface of the abutment proximal portion being substantially continuous or flush with the tapered outer surface of the proximal segment. In that embodiment of the implant wherein the proximal segment of the implant proximal portion has the generally cylindrical outer surface, the attachment of the abutment to the implant in the above-described manner results in the sloped outer surface of the abutment proximal portion extending at a slight angle relative to the cylindrical outer surface of the proximal segment. In accordance with a further embodiment of the present invention, the abutment may have a two-piece construction wherein the abutment distal portion is defined by a shaft member of the abutment, and the abutment proximal portion is collectively defined by the shaft member and a generally frusto-conical sleeve member of the abutment which is attached to the shaft member thereof.

Further in accordance with the present invention, there is provided a method of installing a dental prosthesis into a patient which comprises the initial step drilling a hole into the bony structure of the patient's mouth or oral cavity, and thereafter threading an implant of the dental prosthesis into the hole. An abutment of the dental prosthesis is then attached to the implant in a manner wherein an implant abutment joint is defined between the abutment and the implant. Thereafter, a layer of adhesive is applied to exposed portions of both the abutment and the implant. A crown is then attached to the adhesive covered portions of the abutment and the implant in a manner wherein the implant abutment joint is covered by the crown. The attachment of the crown to the abutment and the implant results in the flow or extension of the adhesive between the crown and the implant in a manner wherein the adhesive seals the implant abutment joint and the joint between the crown and the implant. The step of attaching the abutment to the implant may be accomplished through the use of an adhesive, or via the threadable engagement of the abutment to the implant.

BRIEF DESCRIPTION OF THE DRAWINGS

These, as well as other features of the present invention, will become more apparent upon reference to the drawings wherein.

DETAILED DESCRIPTION OF THE PREFERRED EMBODIMENTS

Figure 1:
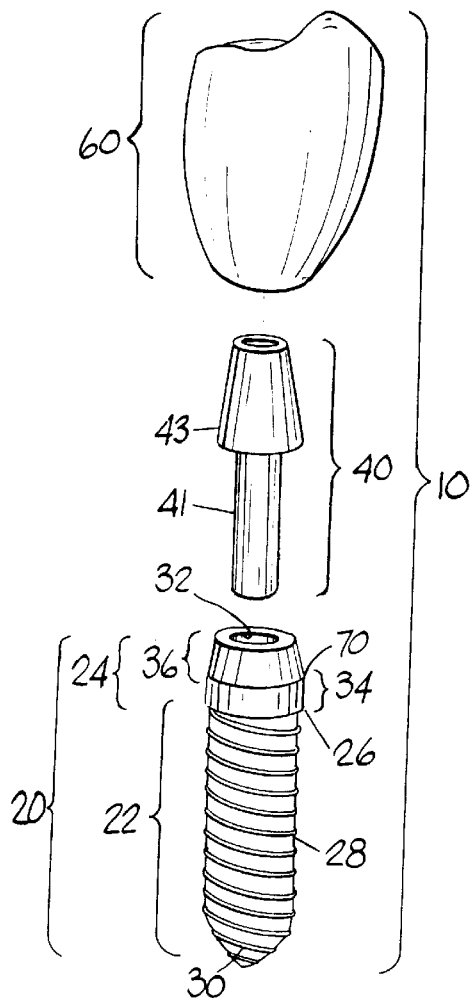
FIG. 1 is a exploded view of a dental prosthesis constructed in accordance with a first embodiment of the present invention, illustrating the implant, abutment, and crown thereof.
Figure 2:
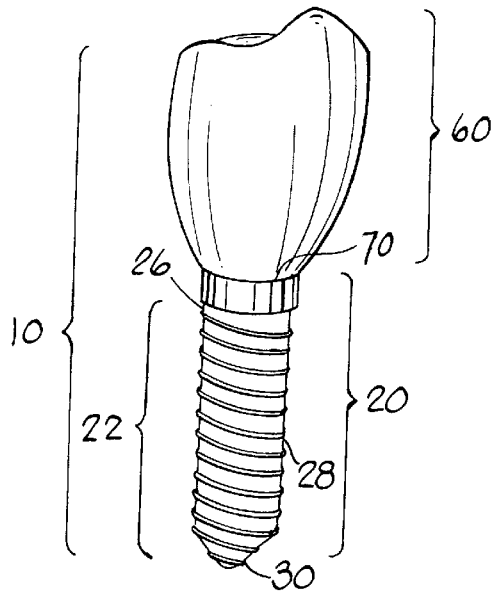
FIG. 2 is a perspective view of the dental prosthesis of the first embodiment in an assembled state.

Referring now to the drawings wherein the showings are for purposes of illustrating preferred embodiments of the present invention only, and not for purposes of limiting the same, FIGS. 1–4 depict a dental prosthesis 10 constructed in accordance with a first embodiment of the present invention. The dental prosthesis 10 comprises an implant 20 which is adapted to be embedded into the bony structure of a patient's mouth or oral cavity. The implant 20 itself includes an elongate implant distal portion 22 which defines an implant distal end 30 and includes external threads 28 formed thereon. The implant distal portion 22 is insertable into the bony structure of the patient's mouth, and more particularly is threaded into a hole drilled into the bony structure as will be described in more detail below.

Figure 3:
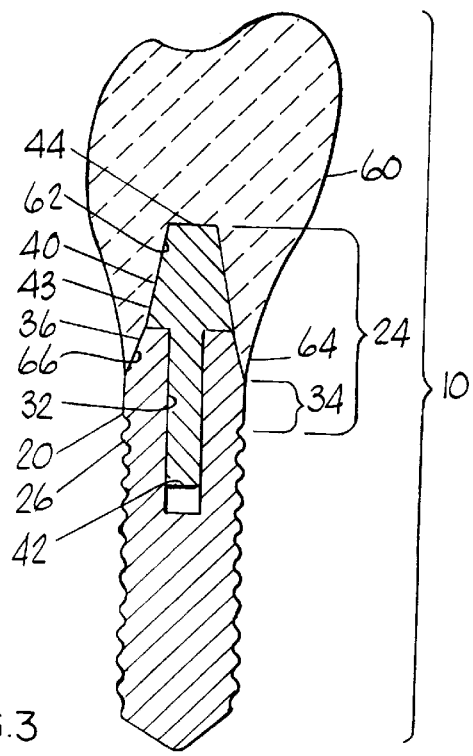
FIG. 3 is a cross-sectional view of the dental prosthesis of the first embodiment in its assembled state as shown in FIG. 2.

In addition to the implant distal portion 22, the implant 20 includes an implant proximal portion 24. The implant proximal portion itself includes a distal segment 34 which has a generally cylindrical outer surface, and a proximal segment 36 which, in the first embodiment, has a beveled or tapered outer surface. The proximal segment 36 also defines an implant proximal end 37. The distal and proximal segments 34, 36 of the implant proximal portion 24 meet at a prosthetic margin 70, with the proximal segment 36 extending radially inward at a slight angle relative to the distal segment 34. The outer diameter of the distal segment 34 slightly exceeds the maximum outer diameter of the implant distal portion 22, thus resulting in the formation of an annular shoulder 26 therebetween. Disposed within the implant proximal end 37 is an implant aperture 32 which has a generally circular cross-sectional configuration, and extends axially through the implant proximal portion 24 to approximately the mid-point of the implant distal portion 22, as seen in FIG. 3.

In the first embodiment, the implant 20 is fabricated from a metallic, biocompatible material such as titanium. Additionally, the implant distal portion 22 may be coated with hydroxylapatite or other suitable biocompatible material to assist in the integration of the implant 20 to the bony structure of the patient's mouth. Additionally, the implant distal portion 22 may be etched with a suitable acid or other solution.

In addition to the implant 20, the dental prosthesis 10 of the first embodiment includes an abutment 40 which is attached to the implant 20 in a manner which will be described in more detail below. The abutment 40 comprises a cylindrically configured, shaft-like abutment distal portion 41 and an abutment proximal portion 43 which has a generally frusto-conical outer surface. As such, the abutment proximal portion 43 has the basic shape of a truncated cone. In the dental prosthesis 10, the abutment distal portion 41 is sized such that the outer diameter thereof is slightly less than the diameter of the implant aperture 32. The abutment 40 is also preferably fabricated from a metallic, biocompatible material, such as titanium.

In the dental prosthesis 10, the attachment of the abutment 40 to the implant 20 is facilitated by the slidable insertion of the abutment distal portion 41 into the implant aperture 32. As will be recognized, the advancement of the abutment distal portion 41 into the implant aperture 32 is terminated by the engagement of the abutment proximal portion 43 to the implant proximal end 37 (i.e., the direct contact therebetween). Importantly, the engagement of the abutment proximal portion 43 to the implant proximal end 37 results in the formation of an implant abutment joint 72 between the abutment 40 and the implant 20.

Figure 4:
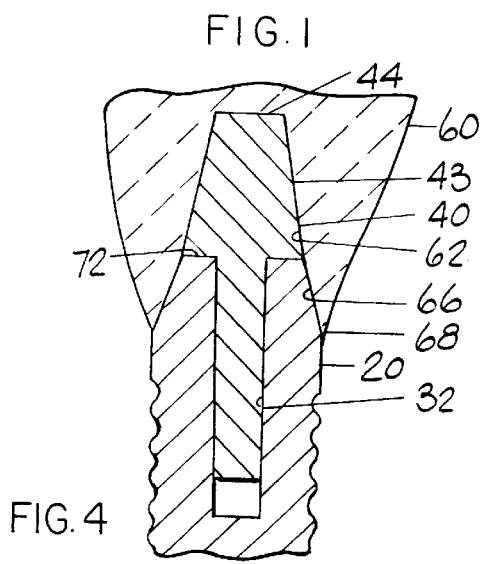
FIG. 4 is a partial cross-sectional view of the dental prosthesis of the first embodiment in its assembled state as shown in FIG. 2.

As seen in FIGS. 3 and 4, the length of the abutment distal portion 41 is such that when the abutment 40 is fully inserted into the implant 20 (i.e., the implant abutment joint 72 is formed), the abutment distal end 42 of the abutment 40 terminates short of the closed bottom end of the implant aperture 32. In this respect, in the dental prosthesis 10 of the first embodiment, the abutment distal portion 41 is secured within the implant aperture 32 through the use of an adhesive. The adhesive may be applied to the abutment distal portion 41 prior to its advancement into the implant aperture 32 and/or injected into the implant aperture 32 prior to the insertion of the abutment distal portion 41 thereinto. The gap defined between the abutment distal end 42 and the closed bottom end of the implant aperture 32 provides an area for adhesive to accumulate and harden, therefore strengthening the bond between the abutment 40 and the implant 20. As further seen in FIGS. 3 and 4, due to the sloped or tapered configurations of the outer surfaces of the proximal segment 36 of the implant proximal portion 24 and outer surface of the abutment proximal portion 43, when the abutment 40 is attached to the implant 22 in the above-described manner, such outer surfaces extend in a generally continuous or flush relation to each other.

The dental prosthesis 10 of the first embodiment further comprises a crown 60 which is fabricated from an inert biocompatible material such as ceramic or metal or both, and is configured in a desired exterior surface configuration in a manner known in the art. The crown 60 includes a crown distal portion 61 which defines a crown distal end 64. Disposed within the crown distal end 64 is a chamfered hole 66 which transitions into a blind hole 62. The chamfered and blind holes 66, 62 collectively define a crown aperture of the crown 60. As further seen in FIGS. 3 and 4, the configuration of the crown aperture, and in particular the chamfered hole 66 partially defining the same, results in the crown distal end 64 having an annular, knife-edge configuration. Additionally, as will be discussed in more detail below, the blind hole 62 is adapted to receive the abutment proximal portion 43 and therefore has a shape which is complementary thereto, with the chamfered hole 66 being adapted to receive the proximal segment 36 of the implant proximal portion 24, and therefore having a shape which is complementary thereto.

In the dental prosthesis 10, the crown is attached to the abutment proximal portion 43 of the abutment 40, and to the proximal segment 36 of the implant proximal portion 24 of the implant 20. Such attachment is accomplished through the use of an adhesive which is applied to the outer surface of the abutment proximal portion 43 including the abutment proximal end 44 defined thereby, and to the outer surface of the proximal segment 36 of the implant proximal portion 24. The crown 60 is then advanced over the abutment 40 and implant 20 such that the abutment proximal portion 43 is snugly received into the blind hole 62 and the proximal segment 36 of the implant proximal portion 24 is snugly received into the chamfered hole 66. The advancement of the crown 60 over the abutment 40 and implant 20 is limited by the engagement of the abutment proximal end 44 against the closed bottom end of the blind hole 62. Importantly, the crown 60 is formed such that when the abutment proximal portion 43 is fully received into the blind hole 62 and the proximal segment 36 fully received into the chamfered hole 66, the knife-edge crown distal end 64 extends to and terminates at the prosthetic margin 70 defined between the distal and proximal segments 34, 36 of the implant proximal portion 24.

When the crown 60 is attached to the abutment 40 and implant 20 in the above-described manner, the crown distal end 64, by virtue of its extension to the prosthetic margin 70, is distal to the implant abutment joint 72, thus resulting in the crown distal portion 61 completely covering the implant abutment joint 72. Additionally, the adhesive used to attach the crown 60 to the abutment proximal portion 43 and proximal segment 36 of the implant proximal portion 24 extends and is disposed between the outer surface of the proximal segment 36 and the inner surface of the crown distal portion 61 which defines the chamfered hole 66. Importantly, the curing or hardening of this adhesive effectively seals the implant abutment joint 72, therefore completely isolating the same from the deteriorous effects of bacterial invasion, plaque and disease. The cured or hardened adhesive also prevents bacterial migration between the crown 60 and implant 20 by sealing the joint between the crown distal portion 61 and proximal segment 36 of the implant proximal portion 24. Also sealed by the cured adhesive is the joint between the crown 60 and the abutment proximal portion 43. Thus, the adhesive serves several essential purposes which include the attachment of the crown 60 to the abutment 40 and implant 20, and sealing off the implant abutment joint 72 and joint between the crown 60 and implant 20 for purposes of preventing the creation of any site(s) in the dental prosthesis 10 which are susceptible to bacterial invasion.

Figure 5:
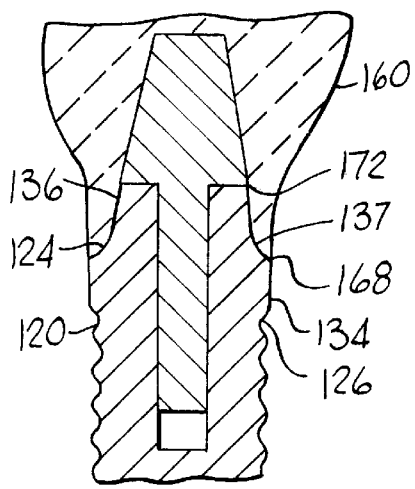
FIG. 5 is a partial cross-sectional view of a dental prosthesis of a second embodiment of the present invention in an assembled state.

Referring now to FIG. 5, there is depicted a dental prosthesis 110 constructed in accordance with a second embodiment of the present invention. The dental prosthesis 110 includes an implant 120 which is substantially similar to the previously described implant 20, and includes an implant distal portion 122 and an implant proximal portion 124 which are separated by an annular shoulder 126 defined therebetween. The implant proximal portion 124 itself includes a distal segment 134 which, like the previously described distal segment 34, has a generally cylindrical outer surface.

In addition to the distal segment 134, the implant proximal portion 124 includes a proximal segment 136 which has a tapered outer surface. However, in contrast to the dental prosthesis 10, the transition between the distal and proximal segments 134, 136 in the dental prosthesis 110 is defined by a curved or arcuate region 137. Forming this arcuate region 137 in the implant 120 allows the distal end 164 of the crown 160 of the dental prosthesis 110 to be rounded and formed with greater thickness, and avoids the knife-edge configuration of the crown distal end 64 in the dental prosthesis 10 of the first embodiment which is more susceptible to breakage or other damage. This alternative configuration for the crown distal end 164 is particularly desirable for crowns made of a ceramic material, in that the previously described knife-edge configuration is generally considered most acceptable for crowns made of gold or other malleable material. The attachment of the crown 160 to the abutment 140 and implant 120 is accomplished in the same manner as previously described in relation to the dental prosthesis 10, thereby resulting in the crown 160 effectively covering the implant abutment joint 172 defined between the abutment 140 and the implant 120.

Figure 6:
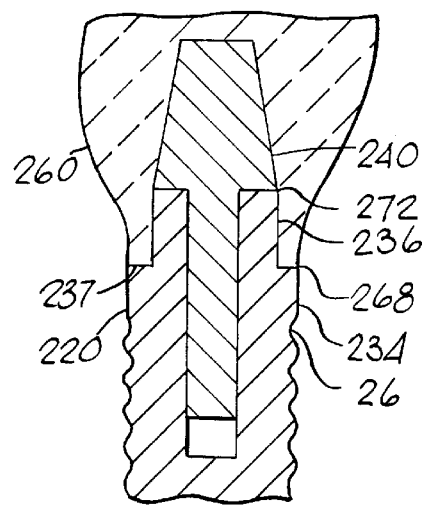
FIG. 6 is a partial cross-sectional view of a dental prosthesis of a third embodiment of the present invention in an assembled state.

Referring now to FIG. 6, there is depicted a dental prosthesis 210 constructed in accordance with a third embodiment of the present invention. The dental prosthesis 210 includes an implant 220 which is substantially similar to the previously described implant 20, and includes an implant distal portion 222 and an implant proximal portion 224 which are separated by an annular shoulder 226 defined therebetween. The implant proximal portion 224 itself includes a distal segment 234 which, like the previously described distal segment 34, has a generally cylindrical outer surface.

In addition to the distal segment 234, the implant proximal portion 224 includes a proximal segment 236 which also has a generally cylindrical outer surface. However, the diameter of the outer surface of the proximal segment 236 is substantially less than the diameter of the outer surface of the distal segment 234. As such, in contrast to the dental prosthesis 10, the transition between the distal and proximal segments 234, 236 in the dental prosthesis 210 is defined by an annular shoulder 237. Forming this shoulder 237 in the implant 220 allows the distal end 234 of the crown 260 of the dental prosthesis 210 to be squared off and formed with greater thickness, thus avoiding the knife-edge configuration of the crown distal end 64 in the dental prosthesis 10 of the first embodiment which is more susceptible to breakage or other damage. This alternative configuration for the crown distal end 264 is also desirable for crowns made of a ceramic material. The attachment of the crown 260 to the abutment 240 and implant 220 is accomplished in the same manner as previously described in relation to the dental prosthesis 10, thereby resulting in the crown 260 effectively covering the implant abutment joint 272 defined between the abutment 240 and the implant 220.

Figure 7:
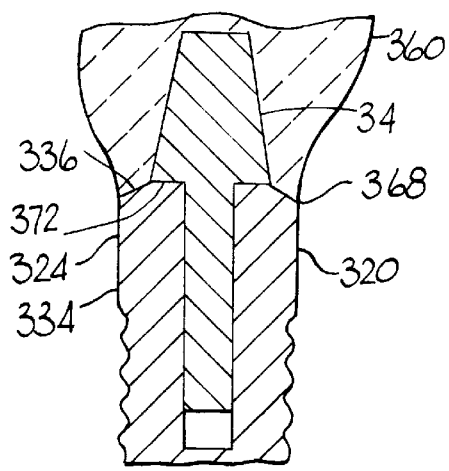
FIG. 7 is a partial cross-sectional view of a dental prosthesis of a fourth embodiment of the present invention in an assembled state.

Referring now to FIG. 7, there is depicted a dental prosthesis 310 constructed in accordance with a fourth embodiment of the present invention. The dental prosthesis 310 includes an implant 320 which is substantially similar to the previously described implant 20, and differs only in that the slope of the tapered outer surface of the proximal segment 336 of the implant proximal portion 324 is substantially greater than that of the outer surface of the proximal segment 36 of the implant proximal portion 24. Such increased slope results in the length of the distal segment 334 of the implant proximal portion 324 exceeding that of the distal segment 34 of the implant proximal portion 24 in the dental prosthesis 10. The attachment of the crown 360 in the dental prosthesis 310 to the implant 320 thereof still results in the crown distal end 364 extending distally beyond the implant abutment joint 372, and the crown 360 thus effectively covering the implant abutment joint 372 when adhesively attached to the abutment 340 and implant 320.

Figure 8:
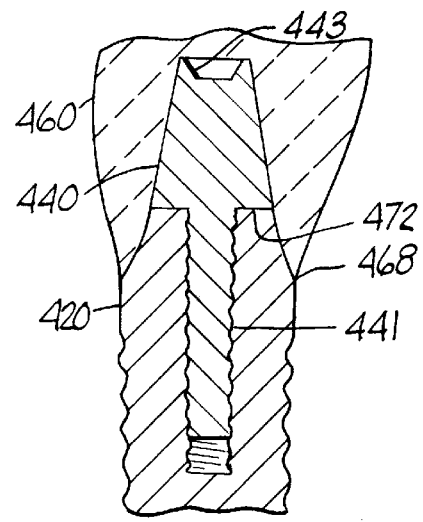
FIG. 8 is a partial cross-sectional view of a dental prosthesis of a fifth embodiment of the present invention in an assembled state.

Referring now to FIG. 8, there is depicted a dental prosthesis 410 constructed in accordance with a fifth embodiment of the present invention. The dental prosthesis 410 is substantially similar to the previously described dental prosthesis 10. However, in the dental prosthesis 410, the abutment distal portion 441 of the abutment 440 is externally threaded, with the abutment proximal portion 443 including a recess disposed within the abutment proximal end for receiving a screwdriver or other implement to rotate the abutment 440. Additionally, the implant aperture 432 of the implant 420 is internally threaded. As such, the attachment of the abutment 440 to the implant 420 is accomplished by the threadable receipt of the abutment distal portion 441 into the implant aperture 432. In the dental prosthesis 410, the attachment of the crown 460 to the abutment 440 and implant 420 results in the crown distal end 464 extending distally beyond the implant abutment joint 472, and the crown 460 covering the implant abutment joint 472 when adhesively attached to the abutment 440 and implant 420.

Figure 9:
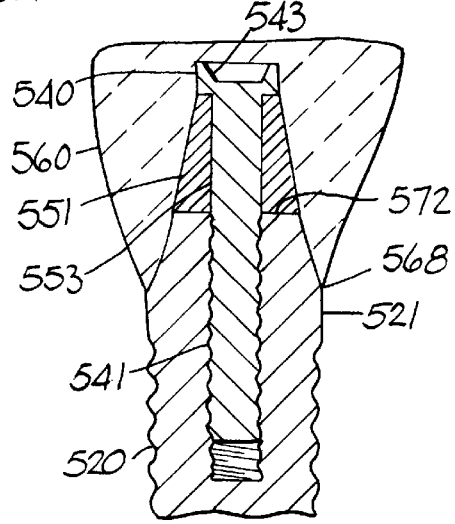
FIG. 9 is a partial cross-sectional view of a dental prosthesis of a sixth embodiment of the present invention in an assembled state.

Referring now to FIG. 9, there is depicted a dental prosthesis 510 constructed in accordance with a sixth embodiment of the present invention. The dental prosthesis 510 is substantially similar to the previously described dental prosthesis 410, except that the abutment 540 of the dental prosthesis 510 is provided with a two-piece construction. More particularly, the abutment 540 comprises a shaft member 553, a portion of which is externally threaded. In addition to the shaft member 553, the abutment 540 includes a sleeve member 551 which has a generally frusto-conical outer surface. The abutment 540 is formed by the attachment of the sleeve member 551 to the shaft member 553. The externally threaded portion of the shaft member 553 defines the abutment distal portion 541 of the abutment 540 which is threadably received into the internally threaded implant aperture 532 of the implant 520. The non-threaded portion of the shaft member 553 and sleeve member 551 collectively define the abutment proximal portion 543 of the abutment 540. The top of the shaft member 553 partially defining the abutment proximal portion 543 includes a recess therein for receiving a screwdriver or other implement to rotate the abutment 540 as is needed to accomplish the threadable engagement thereof to the implant 520. The attachment of the crown 560 of the dental prosthesis 510 to the abutment 540 and implant 520 results in the crown distal end 564 extending distally beyond the implant abutment joint 572, and hence the crown 560 covering the implant abutment joint 572 when adhesively attached to the abutment 540 and implant 520.

Having thus described preferred embodiments of dental prostheses constructed in accordance with the present invention, the method of installing the dental prosthesis 10 of the first embodiment into a patient's mouth or oral cavity will now be described. However, those of ordinary skill in the art will recognize that this installation process is equally applicable to the additional embodiments of the dental prosthesis described above.

The dental prosthesis 10 is used by initially drilling a hole into the bony structure of the patient's mouth or oral cavity. Thereafter, the externally threaded implant distal portion 22 of the implant 20 is embedded into the bony structure by threading the same into the hole previously drilled therein. The implant 20 is preferably embedded into the bony structure in a manner wherein the proximal segment 36 of the implant proximal portion 24 thereof protrudes above the bony structure of the patient's mouth. However, the proximal segment 36 may be disposed below, at, or above the patient's gum line.

Subsequent to the embedding of the implant 20 into the bony structure, the abutment 40 is rigidly attached to the implant 20 in the above-described manner. As indicated above, the attachment of the abutment 40 to the implant 20 may be accomplished through the use of an adhesive, or via the threadable engagement of the abutment 40 and implant 20 to each other.

After the abutment 40 has been attached to the implant 20, a transfer cast is made of the exposed portions of the abutment 40 and implant 20. As will be recognized, these exposed portions include the tapered outer surface of the proximal segment 36 of the implant proximal portion 24, and the frusto-conical outer surface of the abutment proximal portion 43 of the abutment 40. This transfer cast is used to fabricate the crown 60 of the dental prosthesis 10 to insure the complete covering of the exposed portions of the abutment 40 and implant 20 thereby.

Subsequent to the fabrication of the crown, a layer of adhesive is applied to the exposed portions of the abutment 40 and the implant 20 (i.e., the outer surface of the abutment proximal portion 43 and the outer surface of the proximal segment 36). The crown 60 of the dental prosthesis 10 is then attached to those portions of the abutment 40 and the implant 20 which are covered by the adhesive. Such attachment results in the implant abutment joint 72 being completely covered by the crown distal portion 61 of the crown 60, and the extension or flow of the adhesive between the inner surface of the crown distal portion 61 defining the chamfered hole 66 and the tapered outer surface of the proximal segment 36 of the implant proximal portion 24. The adhesive also extends between the inner surface of the crown 60 defining the blind hold 62 and the outer surface of the abutment proximal portion 43. The curing of the adhesive seals the implant abutment joint 72, the crown implant joint formed between the crown 60 and implant 20 (i.e., between the crown distal portion 61 and the outer surface of the proximal segment 36 of the implant proximal portion 24), and the crown abutment joint formed between the crown 60 and abutment 40 (i.e., between the crown 60 and the outer surface of the abutment proximal portion 43).

In the present invention, the covering of the implant abutment joint with the crown and the sealing of the implant abutment joint, the joint between the crown and the implant, and the joint between the crown and the abutment by the adhesive eliminates the susceptibility of such joints to bacterial invasion, plaque contamination or other deteriorations. This results in a number of benefits to the patient. In this respect, bone loss is lessened or eliminated at the implant since disease is unable to thrive in or around these joints. As second major benefit is the anti-rotation of the connection of the crown to the implant achieved by the curing of the adhesive therebetween.

Additional modifications and improvements of the present invention may also be apparent to those of ordinary skill in the art. Thus, the particular combination of parts described and illustrated herein is intended to represent only certain embodiments of the present invention, and is not intended to serve as limitations of alternative devices within the spirit and scope of the invention.

What is claimed is:

1. A dental prosthesis, comprising:

an implant;

an abutment attached to the implant such that an implant abutment joint is defined therebetween; and a crown positioned over the abutment and attached to the implant such that a crown implant joint is defined between the crown and the implant and the implant abutment joint is covered by the crown;

the attachment of the crown to the implant being accomplished through the use of an adhesive which flows into and seals the crown implant joint therebetween.

2. The dental prosthesis of claim 1 wherein:

the implant includes an implant distal portion and an implant proximal portion which defines an implant proximal end having an implant aperture disposed therein;

the abutment includes an abutment proximal portion and an abutment distal portion which is inserted into the implant aperture to facilitate the attachment of the abutment to the implant; and the crown includes a crown distal portion which defines a crown distal end having a crown aperture disposed therein;

the receipt of the abutment proximal portion into the crown aperture resulting in the engagement of the crown distal portion to the implant proximal portion such that the crown implant joint is defined therebetween, the implant abutment joint is covered by the crown distal portion, and the crown implant joint is sealed by the flow of the adhesive thereinto.

3. The dental prosthesis of claim 2 wherein the abutment proximal portion has a generally frusto-conical outer surface.

4. The dental prosthesis of claim 3 wherein:

the implant proximal portion includes a distal segment and a proximal segment having a tapered outer surface which is substantially continuous with the outer surface of the abutment proximal portion when the abutment is attached to the implant; and the crown aperture has a shape which is substantially complementary to the outer surface of the abutment proximal portion and the outer surface of the proximal segment when the abutment is attached to the implant;

the receipt of the abutment proximal portion and the proximal segment into the crown aperture resulting in the engagement of the crown distal portion to the outer surface of the proximal segment such that the crown implant joint is defined therebetween, the implant abutment joint is covered by the crown distal portion, and the crown implant joint is sealed by the flow of the adhesive thereinto.

5. The dental prosthesis of claim 3 wherein:

the implant proximal portion includes a distal segment and a proximal segment having a generally cylindrical outer surface which extends at an angle relative to the outer surface of the abutment proximal portion when the abutment is attached to the implant; and the crown aperture has a shape which is complementary to the outer surface of the abutment proximal portion and the outer surface of the proximal segment when the abutment is attached to the implant;

the receipt of the abutment proximal portion and the proximal segment into the crown aperture resulting in the engagement of the crown distal portion to the outer surface of the proximal segment such that the crown implant joint is defined therebetween, the implant abutment joint is covered by the crown distal portion, and the crown implant joint is sealed by the flow of the adhesive thereinto.

6. The dental prosthesis of claim 2 wherein the abutment distal portion is secured within the implant aperture through the use of an adhesive.

7. The dental prosthesis of claim 2 wherein:

the implant aperture is internally threaded;

the abutment distal portion is externally threaded; and the attachment of the abutment to the implant is facilitated by the threadable receipt of the abutment distal portion into the implant aperture.

8. The dental prosthesis of claim 2 wherein the implant distal portion is externally threaded.

9. The dental prosthesis of claim 2 wherein the abutment comprises:

a shaft member; and a sleeve member attached to the shaft member;

the abutment distal portion being defined by the shaft member and the abutment proximal portion being collectively defined by the shaft member and the sleeve member.

10. The dental prosthesis of claim 9 wherein the shaft member is partially externally threaded.

11. The dental prosthesis of claim 9 wherein the sleeve member has a generally frusto-conical outer surface.

12. The dental prosthesis of claim 11 wherein:

the positioning of the crown over the abutment results in the formation of a crown abutment joint therebetween; and the crown is attached to the implant and to the abutment through the use of the adhesive which flows into and seals the crown implant joint and the crown abutment joint, and seals the implant abutment joint.

13. A dental prosthesis, comprising:

an implant;

an abutment attached to the implant; and a crown positioned over the abutment and attached to the implant such that a crown implant joint is defined between the crown and the implant;

the attachment of the crown to the implant being accomplished through the use of an adhesive which flows into and seals the crown implant joint therebetween.

14. A method of installing a dental prosthesis into a bony structure below a gum line in a patient's oral cavity, the method comprising the steps of:

(a) drilling a hole into the bony structure;

(b) embedding an implant of the dental prosthesis into the hole;

(c) attaching an abutment of the dental prosthesis to the embedded implant such that an implant abutment joint is defined therebetween;

(d) applying a layer of adhesive to at least a portion of the implant; and (e) attaching a crown of the dental prosthesis to that portion of the implant covered by the adhesive such that a crown implant joint is defined between the crown and the implant, the implant abutment joint is covered by the crown, and the crown implant joint is sealed by the flow of the adhesive thereinto.

15. The method of claim 14 wherein step (b) comprises threading the implant into the hole in the bony structure.

16. The method of claim 14 wherein step (c) comprises adhesively securing the abutment to the implant.

17. The method of claim 14 wherein step (c) comprises threadably engaging the abutment to the implant.

18. The method of claim 14 wherein:

step (d) comprises applying the layer of adhesive to portions of the abutment and the implant; and step (e) comprises attaching the crown to those portions of the abutment and the implant covered by the adhesive such that a crown abutment joint is defined between the crown and the abutment, and the crown implant joint, the crown abutment joint, and the implant abutment joint are sealed by the flow of the adhesive into the crown implant joint and the crown abutment joint.

19. The method of claim 18 wherein:

step (d) comprises making a transfer cast of portions of the abutment and the implant prior to the application of the layer of adhesive thereto; and step (e) comprises fabricating the crown from the transfer cast to ensure the complete covering of the adhesive covered portions of the abutment and the implant thereby.

20. The method of claim 14 wherein the implant is embedded into the hole in step (b) so as to be disposed below the gum line such that the attachment of the crown to the implant in step (e) results in the crown implant joint being disposed below the gum line.

* * * * *